United States Patent [19]

Friebe et al.

[11] 4,284,633
[45] Aug. 18, 1981

[54] DERIVATIVES OF XANTHINE

[75] Inventors: Walter-Gunar Friebe, Darmstadt; Max Thiel, Mannheim; Wolfgang Kampe, Heddesheim; Otto-Henning Wilhelms, Weinheim-Rittenweier; Androniki Roesch, Mannheim, all of Fed. Rep. of Germany

[73] Assignee: Boehringer Mannheim GmbH, Mannheim, Fed. Rep. of Germany

[21] Appl. No.: 148,870

[22] Filed: May 12, 1980

[30] Foreign Application Priority Data

May 31, 1979 [DE] Fed. Rep. of Germany ....... 2922159

[51] Int. Cl.³ .............................................. C07D 473/06
[52] U.S. Cl. .................................... 424/253; 544/267; 544/272
[58] Field of Search ............... 544/267, 268, 272, 270; 426/253

[56] References Cited

U.S. PATENT DOCUMENTS

| | | | |
|---|---|---|---|
| 3,642,798 | 2/1972 | Nitta et al. | 544/270 |
| 3,996,361 | 12/1976 | Friebe et al. | 424/253 |
| 4,061,753 | 12/1977 | Bodor et al. | 544/270 |
| 4,086,347 | 4/1978 | Friebe et al. | 424/253 |
| 4,212,866 | 7/1980 | Friebe et al. | 424/253 |

Primary Examiner—Nicholas S. Rizzo
Attorney, Agent, or Firm—Sprung, Felfe, Horn, Lynch & Kramer

[57] ABSTRACT

The present invention provides xanthine derivatives of the general formula:

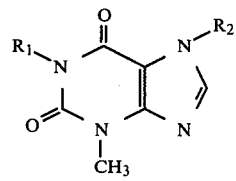

wherein one of the symbols $R_1$ and $R_2$ stands for a methyl radical and the other for a radical of the general formula:

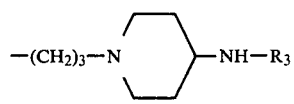

wherein $R_3$ is a hydrogen atom or an acyl radical; and the pharmacologically acceptable salts thereof. The present invention also provides processes for the preparation of these compounds and pharmaceutical compositions containing them and is also concerned with the use thereof for the preparation of pharmaceutical compositions for the treatment of allergies.

9 Claims, No Drawings

DERIVATIVES OF XANTHINE

The present invention is concerned with new derivatives of xanthine, processes for the preparation thereof and pharmaceutical compositions containing them.

U.S. patent application Ser. No. 006,050 filed Jan. 24, 1979 now U.S. Pat. No. 4,212,866 describes purine derivatives with anti-allergic, anti-inflammatory and anti-oedematous action which are derived from adenine or from adenine derivatives substituted on the nitrogen atom in the 6-position.

We have now found that similar derivatives of xanthine inhibit allergic bronchial obstructions in low dosages, weaken allergic skin reactions even after oral administration and display anti-histamine effects.

Thus, according to the present invention, there are provided piperidinoalkyl derivatives of xanthine of the general formula:

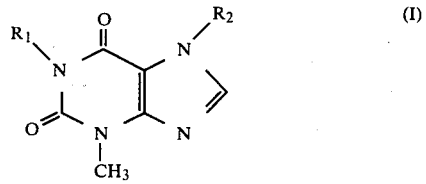

wherein on of the symbols $R_1$ and $R_2$ stands for a methyl radical and the other for a radical of the general formula:

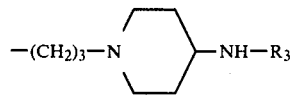

wherein $R_3$ is a hydrogen atom or an acyl radical; as well as the salts thereof with pharmacologically acceptable acids.

The present invention is also concerned with pharmaceutical compositions containing compounds of general formula (I), as well as the use of compounds of general formula (I) for the production of such compositions.

The acyl radicals of the substituent $R_3$ can be lower alkanoyl radicals, which can be substituted one or more times by halogen or by aryl, lower alkenyl radicals substituted by aryl, preferably the cinnamoyl radical, or carbocyclic or heterocyclic aroyl radicals which can be substituted by halogen, hydroxyl, lower alkyl, lower alkoxy, lower alkoxycarbonyl, lower acyloxy, carboxyl, nitro, amino, nitrilo, trifluoromethyl, carbamoyl or benzyl.

The term "lower" in the references to lower alkanoyl, lower alkenoyl, lower alkyl, lower alkoxycarbonyl and lower acyloxy means radicals with up to 8, preferably up to 6 and especially up to 4 carbon atoms, the radicals being straight-chained or branched.

The heterocyclic aroyl radical can be, for example, a furancarbonyl, thiophenecarbonyl or pyridinocarbonyl radical and the carbocyclic aroyl radical can be, for example, a benzoyl radical.

Furthermore, $R_3$ can also represent the acid residue of a cycloalkylcarboxylic acid, cycloalkyl preferably being cyclopropyl, cyclobutyl, cyclopentyl, cyclohexyl or cycloheptyl.

Furthermore, an acyl radical $R_3$ can also be an acid residue of a sulphonic acid, for example, benzenesulphonic acid or methanesulphonic acid. The term "aryl" in the definition of the substituent $R_3$ preferably means a phenyl or naphthyl radical.

The halogen atoms can be fluorine, chlorine or bromine atoms.

Apart from the compounds mentioned in the examples, the present invention also provides, in particular, all compounds which display every possible combination of the substituents mentioned in the examples.

The compounds according to the present invention of general formula (I) can be prepared in known manner by reacting a compound of the general formula:

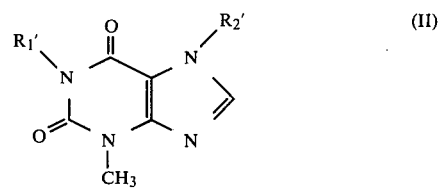

wherein one of the symbols $R'_1$ and $R'_2$ stands for a methyl radical and the other is a hydrogen atom, with a compound of the general formula:

wherein X and Y are reactive residues, and with a compound of the general formula:

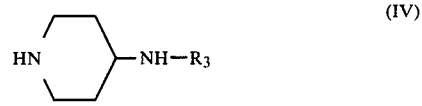

wherein $R_3$ has the same meaning as above, whereafter, if desired, the substituent $R_3$ is replaced by a different substituent $R_3$ by saponification and/or subsequent acylation with a compound of the general formula $R_3$—Z, wherein Z is a reactive residue, if desired a nitro group is hydrogenated to give an amino group and, if desired, the reaction product obtained is converted into a pharmacologically acceptable salt.

The reactive residues X and Y in the compounds of general formula (III) can be, for example, chlorine or bromine atoms or mesyloxy or tosyloxy radicals.

The reactive residues Z can be all residues which are used in peptide chemistry for the activation of carboxylic acids, for example, halogen atoms, the azido group and alkoxy, aryloxy and acyloxy radicals.

The process according to the present invention can be carried out, for example, by first condensing a compound of general formula (III) with a compound of general formula (IV) and isolating the reaction product thus obtained. This intermediate is then reacted with a compound of general formula (II). The reaction is preferably carried out in an alkaline medium and more preferably in a lower alcohol, for example isopropanol in the presence of sodium isopropanolate.

According to another variant of the process, a compound of general formula (II) is first reacted with a compound of general formula (III). Subsequently, the reaction mixture obtained is reacted with a compound of general formula (IV) to give the desired end product of general formula (I).

A subsequent conversion of a group $R_3$ in a compound of general formula (I) into another group $R_3$ can take place, for example, as an exchange of an acyl radical $R_3$ for a different radical $R_3$. For this purpose, a compound of general formula (I) is first saponified in an acid medium and the intermediate obtained acylated by known methods, preferably in the presence of an acid-binding agent. The [3-(4-aminopiperidino)-propyl]-xanthine derivatives obtained as intermediates are also new compounds.

Furthermore, in compounds of general formula (I) in which the acyl radical $R_3$ contains a nitro group, the nitro group can be converted by known methods into an amino group, for example by catalytic hydrogenation.

Compounds of general formulae (II), (III) and (IV) are known from the literature and can easily be prepared from known compounds using well-known methods.

The pharmacologically acceptable salts can be obtained in the usual manner, for example by neutralization of compounds of general formula (I) with non-toxic inorganic or organic acids, for example, hydrochloric acid, sulphuric acid, phosphoric acid, hydrobromic acid, acetic acid, lactic acid, citric acid, malic acid, salicylic acid, malonic acid, maleic acid or succinic acid.

The new compounds of general formula (I) according to the present invention and the salts thereof can be administered enterally and parenterally in liquid or solid form. Thus, the present invention also provides pharmaceutical compositions comprising at least one of the new compounds in admixture with a solid or liquid pharmaceutical diluent or carrier. Use can be made of all the conventional forms of administration, for example, tablets, capsules, dragees, syrups, solutions, suspensions and the like. As injection medium, it is preferred to use water which contains the conventional additives for injection solutions, such as stabilizing agents, solubilizing agents and buffers. Additives of this kind include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Liquid carrier materials for injection solutions must be sterile and are preferably placed into ampules. Solid carrier materials include, for example, starch, lactose, mannitol, methyl cellulose, talc, highly dispersed silicic acids, high molecular weight fatty acids (such as stearic acid), gelatin, agar-agar, calcium phosphate, magnesium stearate, animal and vegetable fats and solid high molecular weight polymers (such as polyethylene glycols). Compositions suitable for oral administration can, if desired, contain flavoring and sweetening agents.

The dosage administered depends upon the age, the state of health and the weight of the recipient, upon the extent of the disease, the nature of other treatments possibly carried out simultaneously, the frequency of the treatments and the nature of the desired action. The daily dosage of the active compounds is usually from about 0.1 to 50 mg./kg. of body weight. Normally, from 0.5 to 40 and preferably from 1.0 to 20 mg./kg./day, in one or more applications per day, are effective for obtaining the desired results.

The following examples are given for the purpose of illustrating the present invention:

EXAMPLE 1

7-{3-[4-(4-Fluorobenzamido)-piperidino]-propyl}-theophylline 3.6 g. (0.02 mol) Theophylline are added to a solution of 0.46 g. (0.02 mol) sodium in 100 ml. isopropanol. The reaction mixture is heated under reflux for 10 minutes, cooled and 6.5 g. (0.022 mol) 3-[4-(4-fluorobenzamido)-piperidino]-propyl chloride added thereto. After stirring the reaction mixture under reflux for 6 hours, it is allowed to cool, filtered and the residue is washed with 2 N aqueous sodium hydroxide solution and water and recrystallized from ethyl acetate. There are obtained 5.8 g. 7-{3-[4-(4-fluorobenzamido)-piperidino]-propyl}-theophylline (66% of theory); m.p. 192°–193° C.

EXAMPLE 2

The following compounds are obtained in a manner analogous to that described in Example 1:

| designation | yield % | m.p. °C. (solvent) |
|---|---|---|
| (a) 7-[3-(4-benzamidopiperidino)-propyl]-theophylline from theophylline and 3-(4-benzamido-piperidino)-propyl chloride | 42 | 177–178 (ethyl acetate/ ligroin) |
| (b) 7-{3-[4-(4-t-butyl-benzamido)-piperidino]-propyl}-theophylline from theophylline and 3-[4-(4-t-butyl-benzamido)-piperidino]-propyl chloride | 47 | 163–165 (ethyl acetate/ ligroin) |
| (c) 7-[3-(4-acetamidopiperidino)-propyl]-theophylline from theophylline and 3-(4-acetamido-piperidino)-propyl chloride | 25 | 155–157 (ethyl acetate/ ligroin) |
| (d) 7-{3-[4-(2-methylbenzamido)-piperidino]-propyl}-theophylline from theophylline and 3-[4-(2-methyl-benzamido)-piperidinopropyl chloride | 37 | 182–183 (isopropanol) |
| (e) 7-[3-(4-phenylacetamido-piperidino)-propyl]-theophylline from theophylline and 3-(4-phenyl-acetamidopiperidino)-propyl chloride | 36 | 158–160 (methanol/ diethyl ether) |
| (f) 1-[3-(4-benzamidopiperidino)-propyl]-theobromine from theobromine and 3-(4-benzamido-piperidino)-propyl chloride | 43 | 172–173 (isopropanol) |
| (g) 1-{3-[4-(4-fluorobenzamido)-piperidino]-propyl}-theobromine from theobromine and 3-[4-(4-fluoro-benzamido)-piperidino]-propyl chloride | 48 | 196–198 (ethyl acetate) |
| (h) 7-{3-[4-(2-methoxybenzamido)-piperidino]-propyl}-theophylline hydrochloride from theophylline and 3-[4-(2-methoxy-benzamido)-piperidino]-propyl chloride | 38 | 254–255 (methanol) |

EXAMPLE 3

7-{3-[4-(Furan-2-carbonylamido)-piperidino]-propyl}-theophylline.

A solution of 7.8 g. (0.06 mol) furan-2-carbonyl chloride in 30 ml. tetrahydrofuran is added dropwise to a mixture of 8.0 g. (0.025 mol) 7-[3-(4-aminopiperidino)- propyl]-theophylline, 100 ml. 1 N aqueous sodium hydroxide solution and 50 ml. tetrahydrofuran, whereafter the reaction mixture is stirred for 5 hours at ambient temperature, filtered and the solid product recrystallized from methanol. There are obtained 5.0 g. 7-{3-[4-(furan-2-carbonylamido)-piperidino]-propyl}-theophylline (49% of theory); m.p. 195°–196° C.

The 7-[3-(4-aminopiperidino)-propyl]-theophylline used as reaction component can be obtained in the following manner:

A mixture of 15.0 g. (0.1 mol) 4-oximinopiperidine hydrochloride, 55 ml. (0.4 mol) triethylamine and 11 ml. (0.11 mol) 1-bromo-3-chloropropane is heated under reflux for 16 hours, cooled, filtered and the filtrate evaporated. There are obtained 15.8 g. 3-(4-oximinopiperidino)-propyl chloride (84% of theory) in the form of an oil.

26.6 g. (0.15 mol) Theophylline are added to a solution of 3.4 g. (0.15 mol) sodium in 350 ml. isopropanol. The reaction mixture is heated under reflux for 10 minutes, 28.0 g. (0.15 mol) 3-(4-oximinopiperidino)-propyl chloride are added thereto, the reaction mixture is heated under reflux for 16 hours and evaporated. The residue is taken up in methylene chloride, washed with water and evaporated. After trituration with diethyl ether, there are obtained 28.5 g. 7-[3-(4-oximinopiperidino)-propyl]-theophylline (57% of theory); m.p. 167°–170° C.

A solution of 6.7 g. (0.02 mol) of the above compound in 150 ml. methanol and 150 ml. tetrahydrofuran is hydrogenated, with the addition of 5 ml. Raney nickel, at ambient temperature and 1 bar hydrogen pressure. After termination of the take up of hydrogen, the reaction mixture is filtered and the filtrate evaporated. There are obtained 6.3 g. 7-[3-(4-aminopiperidino)-propyl]-theophylline (90% of theory) in the form of an oil.

EXAMPLE 4

The following compounds are obtained in a manner analogous to that described in Example 3:

| designation | yield % | m.p. °C. (solvent) |
|---|---|---|
| (a) 7-{3-[4-(2-hydroxybenzamido)-piperidino]-propyl}-theophylline from 7-[3-(4-aminopiperidino)-propyl]-theophylline and salicylic acid chloride | 38 | 210–213 (isopropanol) |
| (b) 7-[3-(4-cyclopropancarbonylamido-piperidino)-propyl]-theophylline from 7-[3-(4-aminopiperidino)-propyl]-theophylline and cyclopropane-carboxylic acid chloride | 42 | 182–183 (methanol) |
| (c) 7-{3-[4-(nitrobenzamido)-piperidino]-propyl}-theophylline from 7-[3-(4-aminopiperidino)-propyl]-theophylline and 4-nitrobenzoyl chloride | 44 | 220–222 (methanol) |
| (d) 7-{3-[4-(thiophene-2-carboxamido)-piperidino]-propyl}-theophylline from 7-[3-(4-aminopiperidino)-propyl]-theophylline and thiophene-2-carbonyl chloride | 68 | 246–248 (methanol) |

EXAMPLE 5

7-{3-[4-(4-Aminobenzamido)-piperidino]-propyl}-theophylline.

A mixture of 4.8 g. (0.01 mol) 7-}3-[4-(4-nitrobenzamido)-piperidino]-propyl}-theophylline (see Example 4c), 150 ml. methanol, 150 ml. tetrahydrofuran and 3 ml. Raney nickel is hydrogenated at ambient temperature and 1 bar hydrogen pressure. Thereafter, the reaction mixture is filtered, the filtrate is evaporated and the residue is taken up in dilute hydrochloric acid, extracted with diethyl ether, rendered alkaline and filtered. After recrystallization from methanol, there are obtained 2.7 g. 7-{3-[4-(4-aminobenzamido)-piperidino]-propyl}-theophylline (60% of theory); m.p. 203°–205° C.

EXAMPLE 6

7-[3-(4-Benzamidopiperidino)-propyl]-theophylline hydrochloride.

A solution of 1.0 g. 7-[3-(4-benzamidopiperidino)-propyl]-theophylline (see Example 2a)) in 20 ml. ethyl acetate is mixed with excess ethereal hydrogen chloride solution, filtered and the precipitate washed with acetone and diethyl ether. There is obtained 0.95 g. 7-[3-(4-benzamidopiperidino)-propyl]-theophylline hydrochloride (88% of theory), which has a melting point above 290° C.

EXAMPLE 7

| Tablets containing active material. | | |
|---|---|---|
| | for 1 tablet | for 100,000 tablets |
| I. Active material [7-{3-[4-(2-hydroxybenzamido)-piperidino]-propyl}-theophylline] | 10.000 mg. | 1.000 kg. |
| lactose | 67.000 mg. | 6.700 kg. |
| corn starch | 35.000 mg. | 3.500 kg. |
| II. polyvinylpyrrolidone (M.W. 30,000) | 3.000 mg. | 0.300 kg. |
| III. sodium carboxymethyl-amylopectin | 4.000 mg. | 0.400 kg. |
| cellulose powder | 20.000 mg. | 2.000 kg. |
| magnesium stearate | 1.000 mg. | 0.100 kg. |
| | 140.000 mg. | 14.000 kg. |
| water for granulating | | 1.000 kg. |

Production: The substances I are granulated with an aqueous solution of II, dried and sieved. The granulate is mixed with the substances III to give a tabletting mass. Tabletting is carried out to give tablets of 7 mm. diameter and 140 mg. weight.

The foregoing compounds can be used as such or they can be converted to salts with pharmacologically acceptable acids. They can be administered orally, as pills, tablets, capsules, powders and the like. The preferred form of oral administration is a tablet containing 10 to 300 mg of active compound, which nearly complies with the typical daily dosage. A preferred dosage is 30 to 100 mg.

The compounds can also be administered parenterally. Injection solutions containing 0,05 to 50 mg/ml of injection solution are administered.

The superior activity of the novel compounds is shown by comparing the inhibition of antigen induced bronchospasms in passively sensitized guinea pigs. Specifically, tests were run as follows:

Preparation of Antiserum

The antigen is twice recrystallized egg albumin. Equal volumes of saline solution of antigen (5 mg/ml) and Freund's complete adjuvant were emulsified and 0.15 ml injected into each hind foot of adult male guinea pigs (Davies and Johnson: Int. Arch. Allergy 41,648–654 (1971)).

The animals were bled and the pooled serum stored at −20° C.

Passive sensitization

Injections of 0.5 ml antiserum of 1:50 dilution were given i.v. 24–48 h before challenge.

Guinea pigs were anaesthetized with pentobarbital sodium (40 mg/kg i.p.). Cannulae were tied into the trachea and the jugular vein and the lung inflated with a pump at a rate of 72 strokes/min and a constant stroke volume of 6–8 ml.

Bronchospasm, provoked by injecting ovalbumin i.v. was measured as described by Konzett, H. and R. Rössler, "Versuchsanordnung und Untersuchungen an der Bronchialmuskulatur" Naunyn-Schmiedebergs, Arch. exp. Path. Pharmak. 195, 71–74 (1940) and modified by Collier, H. O. J., J. A. Holgate and M. Schachter: "The Bronchoconstrictor Action of Bradykinin in the Guinea-Pig" Brit. J. Pharmacol. 15, 290 (1960).

The drugs were applied intravenously 5 minutes before the antigen.

For calculation the following formula was used:

$$\% \text{ Bronchospasm} \frac{b-a}{m-a} \times 100$$

b = Bronchospasm after antigen injection, measured in mm from tracing
m = maximum height of tracing in mm with arm of the treachea-cannula clamped
a = pre injection height of the tracing in mm
% inhibition of bronchospasm was calculated by comparing control groups with drug pretreated groups 3 minutes after antigen application.

The results obtained, statistically confirmed using the t-test, are set forth in the following table:

TABLE
Inhibition of antigen induced bronchospasm (Br Sp) in passively sensitized guinea pigs

| Example | dose mg/kg i.v. | % inhibition Br Sp % |
|---|---|---|
| (2c) | 0.38 | 37 |
| (2e) | 0.38 | 68 |
| (4a) | 0.1 | 82 |
| (4d) | 0.1 | 38 |
| (2d) | 0.1 | 60 |
| Aminophylline | 24 | 29 |

Aminophylline = 2 Mols Theophylline + 1 Mol Ethylenediamine

It will be appreciated that the instant specification and examples are set forth by way of illustration and not limitation, and that various modifications and changes may be made without departing from the spirit and scope of the present invention.

What is claimed is:

1. A xanthine derivative of the formula

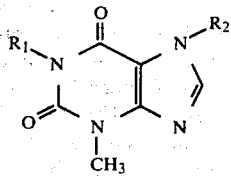

in which
one of $R_1$ and $R_2$ is a methyl radical and the other a radical of the formula

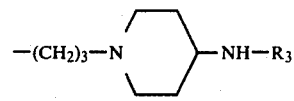

$R_3$ is a hydrogen atom or a lower alkanoyl radical containing up to 8 carbon atoms and which can be substituted by halogen, phenyl or naphthyl, an alkenoyl radical containing up to 8 carbon atoms which can be substituted by phenyl or naphthyl, a phenyl- or alkyl-sulphonyl radical, or a $C_3$–$C_7$-cycloalkylcarbonyl, furancarbonyl, thiophenecarbonyl, pyridinocarbonyl or benzoyl radical which can be substituted by halogen, hydroxyl, $C_1$–$C_8$-alkyl, lower $C_1$–$C_8$-alkoxy, $C_1$–$C_8$-alkoxycarbonyl, $C_1$–$C_8$-alkanoyloxy, carboxyl, nitro, amino, nitrilo, trifluoromethyl, carbamoyl or benzyl,
or a pharmacologically acceptable salt thereof.

2. A xanthine derivative or salt thereof according to claim 1, in which said derivative is 7-[3-(4-acetamidopiperidino)-propyl]-theophylline.

3. A xanthine derivative or salt thereof according to claim 1, in which said derivative is 7-{3-[4-(2-methylbenzamido)-piperidino]-propyl}-theophylline.

4. A xanthine derivative or salt thereof according to claim 1, in which said derivative is 7-[3-(4-phenylacetamidopiperidino)-propyl]-theophylline.

5. A xanthine derivative or salt thereof according to claim 1, in which said derivative is 7-{3-[4-(2-hydroxybenzamido)-piperidino]-propyl}-theophylline.

6. A xanthine derivative or salt thereof according to claim 1, in which said derivative is 7-{- 3-[4-(thiophene-2-carboxamido)-piperidino]-propyl}-theophylline.

7. An anti-allergic composition of matter comprising an anti-allergically effective amount of a xanthine derivative or salt thereof according to claim 1 in admixture with a pharmaceutically acceptable diluent.

8. A method of inhibiting an allergic response in a patient comprising administering to such patient an anti-allergically effective amount of a xanthine derivative or salt thereof according to claim 1.

9. The method according to claim 8 in which said derivative is
7-[3-(4-acetamidopiperidino)-propyl]-theophylline,
7-{3-[4-(2-methylbenzamido)-piperidino]-propyl}-theophylline,
7-[3-(4-phenylacetamidopiperidino)-propyl]-theophylline,
7-{3-[4-(2-hydroxybenzamido)-piperidino]-propyl}-theophylline, or
7-{3-[4-(thiophene-2-carboxamido)-piperidino]-propyl}-theophylline.

* * * * *